(12) United States Patent
Delisle et al.

(10) Patent No.: US 12,161,693 B2
(45) Date of Patent: Dec. 10, 2024

(54) METHODS OF MAKING STABLE SILK FIBROIN FORMULATIONS

(71) Applicant: Cocoon Biotech Inc., Mansfield, MA (US)

(72) Inventors: Scott Delisle, Mansfield, MA (US); Michael Santos, Mansfield, MA (US)

(73) Assignee: Cocoon Biotech Inc., Mansfield, MA (US)

(*) Notice: Subject to any disclaimer, the term of this patent is extended or adjusted under 35 U.S.C. 154(b) by 0 days.

(21) Appl. No.: 17/720,601

(22) Filed: Apr. 14, 2022

(65) Prior Publication Data

US 2022/0331400 A1  Oct. 20, 2022

Related U.S. Application Data

(60) Provisional application No. 63/175,024, filed on Apr. 14, 2021.

(51) Int. Cl.
| | | |
|---|---|---|
| *A61K 9/08* | (2006.01) |
| *A61K 9/00* | (2006.01) |
| *A61K 38/17* | (2006.01) |
| *A61K 47/02* | (2006.01) |

(52) U.S. Cl.
CPC ........ *A61K 38/1767* (2013.01); *A61K 9/0048* (2013.01); *A61K 9/08* (2013.01)

(58) Field of Classification Search
CPC ....... A61K 38/1767; A61K 9/08; A61K 47/02
See application file for complete search history.

(56) References Cited

U.S. PATENT DOCUMENTS

| | | |
|---|---|---|
| 4,806,355 A | 2/1989 | Goosen et al. |
| 4,937,370 A | 6/1990 | Sabatelli |
| 4,999,186 A | 3/1991 | Sabatelli et al. |
| 5,015,476 A | 5/1991 | Cochrum et al. |
| 5,073,371 A | 12/1991 | Turner et al. |
| 5,073,372 A | 12/1991 | Turner et al. |
| 5,087,372 A | 2/1992 | Toyotomo et al. |
| 5,093,489 A | 3/1992 | Piamantoglou |
| 5,263,992 A | 11/1993 | Guire |
| 5,270,419 A | 12/1993 | Domb |
| 5,576,881 A | 11/1996 | Doerr et al. |
| 5,827,508 A | 10/1998 | Tanner et al. |
| 5,902,800 A | 5/1999 | Green et al. |
| 5,935,556 A | 8/1999 | Tanner et al. |
| 5,968,485 A | 10/1999 | Robinson |
| 5,972,316 A | 10/1999 | Robinson |
| 6,127,143 A | 10/2000 | Gunasekaran |
| 6,245,537 B1 | 6/2001 | Williams et al. |
| 6,267,776 B1 | 7/2001 | O'Connell |
| 6,302,848 B1 | 10/2001 | Larson et al. |
| 6,310,188 B1 | 10/2001 | Mukherjee |
| 6,325,810 B1 | 12/2001 | Hamilton et al. |
| 6,337,198 B1 | 1/2002 | Levene et al. |
| 6,372,244 B1 | 4/2002 | Antanavich et al. |
| 6,379,690 B2 | 4/2002 | Blanchard et al. |
| 6,395,734 B1 | 5/2002 | Tang et al. |
| 9,394,355 B2 | 7/2016 | Lawrence et al. |
| 9,907,836 B2 | 3/2018 | Lawrence et al. |
| 2011/0167602 A1 | 7/2011 | Altman et al. |
| 2016/0096878 A1 | 4/2016 | Lawrence et al. |
| 2017/0031287 A1 | 2/2017 | Teniguchi et al. |
| 2017/0333351 A1 | 11/2017 | Kaplan et al. |
| 2018/0193429 A1 | 7/2018 | Lawrence et al. |
| 2021/0101946 A1 | 4/2021 | Lo et al. |

FOREIGN PATENT DOCUMENTS

| | | |
|---|---|---|
| WO | 200006110 A1 | 2/2000 |
| WO | 2001090389 A2 | 11/2001 |
| WO | 2005012606 A2 | 2/2005 |
| WO | 2014049129 A1 | 4/2014 |
| WO | 2014145002 A2 | 9/2014 |
| WO | 2016029034 A1 | 2/2016 |
| WO | 2016059611 A1 | 4/2016 |
| WO | 2016067189 A1 | 5/2016 |
| WO | 2017106631 A1 | 6/2017 |
| WO | 2017123383 A2 | 7/2017 |
| WO | 2017139684 A1 | 8/2017 |

(Continued)

OTHER PUBLICATIONS

International Search Report and Written Opinion for International Application PCT/US2022/024731; International Filing Date: Apr. 14, 2022; Date of Mailing: Jul. 8, 2022; 6 pages.
Abdel-Naby, W. et al.; "Silk-Derived Protein ENhances Corneal Epithelial Migration, Adhesion, and Proliferation"; Cornea, vol. 58, Issue No. 3; 2017; pp. 1425-1433.
Abdel-Naby, W. et al.; "Treatment with solubilized Silk-Derived Protein (SDP) enhances rabbit corneal epithelial wound healing"; PLoS One, vol. 12, Issue No. 11; 2017; 15 pages; https://doi.org/10.1371/journal.pone.0188154.
Cao, Y. et al.; "Biodegradation of Silk Biomaterials"; International Journal of Molecular Sciences, vol. 10; 2009; pp. 1514-1524; doi:10.3390/ijms10041514.
Deputch, T. et a.; "Silk Materials Functionalized via Genetic Engineering for Biomedical Applications"; Materials, vol. 10, Issue No. 12; 2017; 1417; doi:10.3390/ma10121417.
Kim, C. et al.; "Effects of silk fibroin in murine dry eye"; Scientific Reports, vol. 7; 2017; 44364; doi:10.1038/srep44364.

(Continued)

*Primary Examiner* — Julie Ha
(74) *Attorney, Agent, or Firm* — Karen A. LeCuyer; DeWitt LLP

(57) ABSTRACT

The present disclosure describes methods of preparing stable, solubilized silk fibroin preparations. The methods include providing a processed silk fibroin preparation. preparing a solution of the processed silk fibroin preparation in an aqueous TRIS buffer to provide a fibroin solution, treating the fibroin solution at least at a first pressure of 0 to 30 psi and a first temperature of 100° C. to 135° C. for a first time of 1 to 90 min to provide the stable. solubilized silk fibroin preparation. The stable, solubilized silk fibroin preparation has a molecular weight that changes by less than 33% during the first and optional second treating step, does not form a gel during the first and optional second treating step, remains clear after the first and optional second treating step, or a combination thereof.

9 Claims, No Drawings

(56) References Cited

FOREIGN PATENT DOCUMENTS

| | | |
|---|---|---|
| WO | 2017200659 A2 | 11/2017 |
| WO | 2018031973 A1 | 2/2018 |
| WO | 2019094700 A1 | 5/2019 |

OTHER PUBLICATIONS

Moshirfar, M. et al.; "Artificial tears potpourri: a literature review"; Clinical Ophthalmology, vol. 8; 2014; pp. 1419-1433.

Price, R. et al.; "Controlled Release from Recombinant Polymers"; Journal of Controlled Release, vol. 190; 2014; pp. 304-313.

Tokareva, O. et al.; "Recombinant DNA production of spider silk proteins"; Microbial Technology, vol. 6, Issue No. 6; 2013; pp. 651-663.

Woltje, M. et al.; "A Fast and Reliable Process to Fabricate Regenerated Silk Fibroin Solution from Degummed Silk in 4 Hours"; International Journal of Molecular Sciences, vol. 22, Issue No. 10565; 2021; 16 pages; DOI: https://doi.org/10.3390/ijms221910565.

Yu, E. et al.; "Development of Biomimetic Thermoplastic Polyurethane/Fibroin Small-Diameter Vascular Grafts via a Novel Electrospinning Approach"; Journal of Biomedical Research Part A, vol. 106, Issue No. 4; 2018; pp. 985-996.

METHODS OF MAKING STABLE SILK FIBROIN FORMULATIONS

CROSS-REFERENCE TO RELATED APPLICATIONS

This application claims priority to U.S. Provisional Application 63/175,024 filed on Apr. 14, 2021, which is incorporated herein by reference in its entirety.

FIELD OF THE DISCLOSURE

The present disclosure relates to methods of making stable silk fibroin formulations.

BACKGROUND OF THE DISCLOSURE

Silk is a naturally occurring polymer. Most silk fibers are derived from silkworm moth (*Bombyx mori*) cocoons and include silk fibroin and sericin proteins. Silk fibroin is a fibrous material that forms a polymeric matrix bonded together with sericin. In nature, silk is formed from a concentrated solution of these proteins that are extruded through silkworm spinnerets to produce a highly insoluble fiber.

Many properties of silk fibroin make it an attractive candidate for products serving a variety of industries. Polymer strength and flexibility has supported classical uses of silk fibroin in textiles and materials, while silk fibroin biocompatibility has gained attention more recently for applications in the fields of medicine and agriculture. Additional uses for silk fibroin in applications related to material science are being explored as technologies for producing and processing silk fibroin advance.

Although a variety of products and uses related to silk fibroin are being developed, there remains a need for methods of producing and processing silk fibroin and formulations containing processed silk fibroin that can meet the demands. The present disclosure addresses these needs by providing methods for producing and processing silk fibroin as well as formulations of silk fibroin-based products useful in a variety of industries.

SUMMARY OF THE DISCLOSURE

In an aspect, the present disclosure provides a method of preparing a stable, solubilized silk fibroin preparation comprising, providing a processed silk fibroin preparation, preparing a solution of 0.1 to 5.0 wt % of the processed silk fibroin preparation in 10 mM to 100 mM aqueous Tris buffer, pH 5.0 to 9.0 to provide a fibroin solution, treating the fibroin solution at a first pressure of 0 to 30 psi, specifically 5 to 30 psi, more specifically 15 to 20 psi and a first temperature of 100° C. to 135° C., specifically 110° C. to 135° C., more specifically 121° C. to 125° C. for a first time of 1 to 90 minutes, specifically 10 to 90 minutes, more specifically 30 to 45 minutes, and optionally treating the fibroin solution at a second pressure of 0 to 30 psi, specifically 5 to 30 psi, more specifically 15 to 20 psi and a second temperature of 100° C. to 135° C., specifically 110° C. to 135° C., more specifically 121° C. to 125° C. for a second time of 1 to 90 minutes, specifically 10 to 90 minutes, more specifically 30 to 45 minutes, to provide the stable, solubilized silk fibroin preparation, wherein the stable, solubilized silk fibroin preparation has a molecular weight that changes by less than 33% during the first and optional second treating step,
does not form a gel during the first and optional second treating step,
remains clear after the first and optional second treating step, or
a combination thereof.

DETAILED DESCRIPTION

Embodiments of the present disclosure relate to formulations comprising processed silk fibroin, and their methods of use. The term "silk" generally refers to a fibrous material formed by insects and some other species that includes tightly bonded protein filaments including fibroin and sericin. Herein, the term "silk" is used in the broadest sense and may embrace any forms, variants, or derivatives of silk discussed.

Silk fibers from silkworm moth (*Bombyx mori*) cocoons include two main components, sericin (usually present in a range of 20-30%) and silk fibroin (usually present in a range of 70-80%). Structurally, silk fibroin forms the center of the silk fibers and sericin acts as the gum coating the fibers. Silk fibroin is an insoluble fibrous protein consisting of layers of antiparallel beta sheets. As used herein, the terms fibroin and silk fibroin are used interchangeably. Its primary structure mainly consists of recurrent serine, alanine, and glycine repeating units. The isoelectric point of fibroin has been determined to be around 4.2. Silk fibroin monomers include a complex of heavy chain (around 350 kDa) and light chain (around 25 kDa) protein components. Typically, the chains are joined by a disulfide bond. With some forms, heavy chain and light chain segments are non-covalently bound to a glycoprotein, p25. During silk processing, fragments of silk fibroin monomers may be produced, including, but not limited to, fragments of heavy and/or light chains. These fragments may retain the ability to form hydrogen bonds with silk fibroin monomers and fragments thereof. Herein, the term "silk fibroin" is used in its broadest sense and embraces silk fibroin polymers, silk fibroin monomers, silk fibroin heavy and light chains, silk fibroin fragments, and variants, derivatives, or mixtures thereof from any of the wild type, genetically modified, or synthetic sources of silk described herein.

In some embodiments, silk fibroin includes silk obtained from a silk producer. Silk producers may be organisms found in nature (referred to herein as "wild type organisms") or they may be genetically modified organisms. There are many species of silk producers in nature capable of producing silk. Silk producers may be insect species, such as silkworms. Some silk producers include arachnid species. In some embodiments, silk producers include species of mollusk. In some embodiments, silk producers are genetically modified organisms. Silk produced by different silk producing species may vary in physical and/or chemical properties. Such properties may include amino acid content, secondary structure (e.g., beta-sheet content), mechanical properties (e.g. elasticity), and others. In some embodiments, the present disclosure provides blends of processed silk from multiple silk producers or other sources (e.g., recombinant or synthetic silk). Such blends may have synergistic properties that are absent from processed silk obtained from single sources or from alternative blends.

In some embodiments, silk fibroin may be obtained from the silkworm species *Bombyx mori*. Other examples of silk producer species include, but are not limited to, *Bombyx mandarina, Bombyx sinesis, Anaphe moloneyi, Anaphe panda, Anaphe reticulate, Anaphe ambrizia, Anaphe carteri, Anaphe venata, Anapha infracta, Antheraea assamensis,*

*Antheraea assama, Antheraea mylitta, Antheraea pernyi, Antheraea yamamai, Antheraea polyphemus, Antheraea oculea, Anisota senatoria, Apis mellifera, Araneus diadematus, Araneus cavaticus, Automeris io, Atticus atlas, Copaxa multifenestrata, Coscinocera hercules, Callosamia promethea, Eupackardia calleta, Eurprosthenops australis, Gonometa postica, Gonometa rufobrunnea, Hyalophora cecropia, Hyalophora euryalus, Hyalophora gloveri, Miranda auretia, Nephila madagascarensis, Nephila clavipes, Pachypasa otus, Pachypasa atus, Philosamia ricini, Pinna squamosa, Rothschildia hesperis, Rothschildia lebeau, Samia Cynthia*, and *Samia ricini*.

As used herein, the term "recombinant silk fibroin" refers to any form of silk fibroin produced using recombinant DNA technology. Recombinant silk fibroin may include amino acid sequences corresponding to silk proteins produced by wild type organisms; amino acid sequences not found in nature; and/or amino acid sequences found in nature, but not associated with silk. In some embodiments, recombinant silk may be encoded by expression plasmids.

In some embodiments, formulations include synthetic silk. As used herein, the term "synthetic silk" refers to silk prepared without the aid of a silk producer. Synthetic silk may be prepared using standard methods of peptide synthesis. Such methods typically include the formation of amino acid polymers through successive rounds of polymerization. Amino acids used may be obtained through commercial sources and may include natural or non-natural amino acids. In some embodiments, synthetic silk polypeptides are prepared using solid-phase synthesis methods. The polypeptides may be linked to resin during synthesis. In some embodiments, polypeptide synthesis may be conducted using automated methods. In some embodiments synthetic silk may be prepared using cell-free peptide synthesis (CFPS).

Preparation of Processed/Purified Silk Fibroin

In order to provide silk fibroin, sericin is removed from raw silk, for example, to provide processed/purified silk fibroin. "Degumming" is the process of removing sericin from a silk starting material such as raw silk, which includes sericin secreted during cocoon formation. Methods of degumming include heating (e.g., boiling) in a degumming solution. As used herein, the term "degumming solution" refers to a composition used for sericin removal that includes at least one degumming agent. As used herein, a "degumming agent" refers to a substance that may be used for sericin removal. Heating in degumming solution may reduce or eliminate sericin from processed silk. In some embodiments, heating in degumming solution includes boiling. Heating in degumming solution may be followed by rinsing to enhance removal of sericin that remains after heating. In some embodiments, raw silk is degummed before further processing or utilization in formulations. In other embodiments, raw silk is further processed or otherwise incorporated into a formulation prior to degumming.

In an aspect, fibroin is produced by providing raw silk (e.g., unpurified silk such as silk yarn), the raw silk comprising fibers containing silk fibroin and sericin. First, the raw silk is degummed in a salt solution, specifically a sodium carbonate solution with a sodium carbonate concentration of 0.02 to 0.5 M sodium carbonate at a temperature of about 60 to about 100° C., and for a time of greater than 60 minutes to about 480 minutes. In a preferred aspect, degumming is performed in 0.5 M sodium carbonate at 85° C. for either 240 or 360 minutes. In an aspect, degumming provides degummed silk fibers having a sericin concentration of 0-0.5 wt %.

After the degumming, the silk fibroin fibers are further processed by dissolving, preferably in aqueous solution. Dissolving preferably includes using 5M to 13M lithium bromide for 1 hour to overnight at 50° C. to 100° C. to provide dissolved silk fibers, or dissolving the degummed silk fibers using a mixture of calcium chloride, ethanol, and water in a molar ratio of 1:2:8 for 1 hour to overnight at 50° C. to 100° C. to provide dissolved silk fibers. In a specific aspect, 10 wt % to 20 wt % silk fibroin is dissolved in 9.3M lithium bromide at 80° C. for 16 hours (overnight).

Solvents used to dissolve processed silk may include a buffer. In some embodiments, solvent used is an organic solvent. Organic solvents include, but are not limited to hexafluoroisopropanol (HFIP), methanol, isopropanol, ethanol, or combinations thereof. In some embodiments, solvents include a mixture of an organic solvent and water or an aqueous solution. Solvents may include water or aqueous solutions. Aqueous solutions may include aqueous salt solutions that include one or more salts. Such salts may include but are not limited to lithium bromide (LiBr), lithium thiocyanate, Ajisawa's reagent, a chaotropic agent, calcium nitrate, or other salts capable of solubilizing silk, including any of those disclosed in U.S. Pat. No. 9,623,147 (the content of which is herein incorporated by reference in its entirety). In some embodiments, solvents used in processed silk solutions include high salt solutions. Ajisawa's reagent comprises a mixture of calcium chloride, ethanol, and water in a molar ratio of 1:2:8 respectively.

In a preferred embodiment, the degummed silk fibroin is dissolved in 5 to 13 M LiBr. The concentration of LiBr may be 9.3 M. Dissolving in LiBr can be done at 80° C. for 16 hours (overnight).

In some embodiments, solvents used in processing silk solutions may include Ajisawa's reagent, as described in Zheng et al. (2016) Journal of Biomaterials Applications 31:450-463, the content of which is herein incorporated by reference in its entirety.

After the silk fibroin fibers are dissolved, they can be diluted prior to further purification. In an aspect, the dissolved silk fibers are diluted in water to provide a concentration of 5 to 20% w/v silk fibroin fibers. Optionally the diluted fibroin solution is filtered through a polypropylene, polyethersulfone, nylon, or cellulose, diatomaceous earth, perlite depth prefilter to remove particulates and provide a clarified silk fiber solution.

The diluted silk fibroin fibers can be purified using dialysis or tangential flow filtration (TFF) using a regenerated cellulose or polyethersulfone filter, and concentrating and recovering processed silk fibroin from the TFF. For example, the silk solution is concentrated 2x, and then diafiltered to remove the chaotropic agents, i.e., lithium bromide/calcium chloride and ethanol. Diafiltration can be performed against water at pH 3.0-11.0, salt solution, i.e., sodium chloride, potassium chloride, (10 mM-500 mM) at pH 3.0-11.0, buffer, i.e., sodium phosphate, potassium phosphate, tromethamine, at 10 mM-250 mM, at pH 3.0-11.0, or buffer containing 10 mM-500 mM salt pH 3.0-11.0. Diafiltration is performed for 5-15 diavolumes, or until a sufficient amount of the chaotropic agent is removed.

In an aspect, molecular weight, specifically number average molecular weight is determined by size exclusion chromatography. In an aspect, the molecular weight of the processed silk fibroin is up to about 350 kDa, but more particularly about 20 to about 50 kDa. For most applications, the molecular weight is 25-42 kDa. For ocular solutions, the molecular weight is 25-50 kDa.

After purification, the silk fibroin is referred to as processed silk fibroin or purified silk fibroin.

Processed silk fibroin is dissolved for a time and temperature to provide a stable, solubilized silk fibroin preparation. The stable, solubilized silk fibroin preparation can then be used to prepare formulations such as pharmaceutical formulations including ocular formulations.

In some embodiments, processed silk preparations are dried to remove solvent. In some embodiments, formulations may be rinsed prior to drying. Methods of drying may include, but are not limited to, air drying, oven drying, lyophilization, spray drying, spray freezing, and vacuum drying. Drying may be carried out to alter the consistency and/or other properties of processed silk preparations. One or more compounds or excipients may be combined with processed silk preparations to improve processed silk recovery and/or reconstitution after the drying process. For example, sucrose may be added to improve silk fibroin recovery and reconstitution from dried solutions. In some embodiments, drying may be carried out in the fabrication of a processed silk format. Examples include, but are not limited to fabrication of fibers, nanofibers, mats, films, foams, membranes, rods, tubes, gels, hydrogels, microspheres, nanospheres, solutions, patches, grafts and powders. In some embodiments, drying processed silk is carried out by oven drying, lyophilizing, and/or air drying.

In some embodiments, processed silk fibroin preparations are freeze dried. Freeze drying may be carried out by lyophilization. Freeze drying may require processed silk preparations to be frozen prior to freeze drying. Freezing may be carried out at temperatures of from about 5° C. and about −85° C. In some embodiments, freeze drying is carried out by lyophilization for up to 75 hours. In some embodiments, lyophilization is used to prepare processed silk formats. Such formats may include, but are not limited to, fibers, nanofibers, mats, films, foams, membranes, rods, tubes, gels, hydrogels, microspheres, nanospheres, solutions, patches, grafts and powders.

Production of Stable, Solubilized Silk Fibroin

Processed silk fibroin may be dissolved for a time and temperature to provide a stable, solubilized silk fibroin preparation. The stable, solubilized silk fibroin preparation can then be used to prepare formulations such as pharmaceutical formulations including ocular formulations.

The length of time used to dissolve processed silk in a solvent, e.g., water, is referred to herein as "dissolution time." Dissolution times for dissolution of processed silk in various solvents, e.g., water, may be from about 1 min to about 5 min, from about 2 min to about 10 min, from about 5 min to about 15 min, from about 10 min to about 25 min, from about 20 min to about 35 min, from about 30 min to about 50 min, from about 45 min to about 75 min, from about 60 min to about 95 min, from about 90 min to about 125 min, from about 120 min to about 175 min, from about 150 min to about 200 min, from about 180 min to about 250 min, from about 210 min to about 350 min, from about 240 min to about 360 min, from about 270 min to about 420 min, from about 300 min to about 480 min, or longer than 480 minutes.

The temperature used to dissolve processed silk fibroin in solvent is referred to herein as "dissolution temperature." Dissolution temperatures used for dissolution of processed silk in solvent may include room temperature to temperatures greater than 200° C. In some embodiments, dissolution includes boiling. In a preferred embodiment, dissolution is carried out by autoclaving.

In an aspect, dissolution of the process silk fibroin is carried out by autoclaving in TRIS (tris(hydroxymethyl) aminomethane)) buffer. It was unexpectedly found herein that autoclaving in TRIS buffer provided improved stability compared to phosphate, borate, carbonate or citrate buffer or no buffer.

Specifically, providing a processed silk fibroin preparation comprises preparing a solution of 0.1 to 5.0 wt % of the processed silk fibroin preparation in 10 mM to 100 mM aqueous TRIS buffer, pH 5.0 to 9.0 to provide a fibroin solution, treating the fibroin solution at a first pressure of 0 to 30 psi, specifically 5 to 30 psi, more specifically 15 to 20 psi and a first temperature of 100° C. to 135° C., specifically 110° C. to 135° C., more specifically 121° C. to 125° C. for a first time of 1 to 90 minutes, specifically 10 to 90 minutes, more specifically 30 to 45 minutes, and optionally treating the fibroin solution at a second pressure of 0 to 30 psi, specifically 5 to 30 psi, more specifically 15 to 20 psi and a second temperature of 100° C. to 135° C., specifically 110° C. to 135° C., more specifically 121° C. to 125° C. for a second time of 1 to 90 minutes, specifically 10 to 90 minutes, more specifically 30 to 45 minutes, to provide the stable, solubilized silk fibroin preparation. As used herein, a stable, solubilized silk fibroin preparation has a molecular weight that changes by less than 33% during the first and optional second treating step, does not form a gel during the first and optional second treating step, remains clear after the first and optional second treating step, or a combination thereof.

In an aspect, the 10 mM to 100 mM aqueous TRIS further comprises 100 mM to 200 mM, specifically 135 mM KCl or NaCl.

In an aspect, the stable, solubilized silk fibroin preparation is an aqueous solution comprising 0.1 to 10% weight/volume silk fibroin.

In another aspect, the stable, solubilized silk fibroin preparation has a molecular weight that changes by less than 33% after standing at room temperature for up to 30, 60 or even 90 days time, does not form a gel after standing at room temperature for at least 2 years time, remains clear after standing at room temperature for at least 2 years time, or a combination thereof.

Mechanical Properties

In some embodiments, the mechanical properties of processed silk fibroin may be altered by modulating physical and/or chemical properties of the processed silk. The mechanical properties include, but are not limited to, mechanical strength, tensile strength, elongation capabilities, elasticity, compressive strength, stiffness, shear strength, toughness, torsional stability, temperature stability, moisture stability, viscosity and reeling rate. In some embodiments, the tensile strength of processed silk is stronger than steel. In some embodiments, the tensile strength of processed silk is stronger than steel. Examples of the physical and chemical properties used to tune the mechanical properties of processed silk include, but are not limited to, the temperature, formulations, silk concentration, β-sheet content, crosslinking, the molecular weight of the silk, the storage of the silk, storage, methods of preparation, dryness, methods of drying, purity, and degumming.

Processed silk fibroin strength and stability are factors for many applications. In some embodiments, processed silk fibroin may be selected based on or prepared to maximize mechanical strength, tensile strength, elongation capabilities, elasticity, flexibility, compressive strength, stiffness, shear strength, toughness, torsional stability, biological stability, resistance to degradation, and/or moisture stability. In some embodiments, processed silk has a non-acidic microenvironment. In some embodiments, the non-acidic microenvironment enhances the stability of processed silk. In some embodiments, the non-acidic microenvironment enhances the stability of therapeutic agents formulated with processed silk. In some embodiments, the tensile strength of processed silk is stronger than steel. In some embodiments, the tensile strength of processed silk is stronger than steel.

Formulations

Formulations may include processed silk fibroin with other components (e.g., excipient, therapeutic agent, microbe, cargo, and/or biological system), wherein each component is present at a specific concentration, ratio, or range of concentrations or ratios, depending on application. In some embodiments, the concentration of processed silk or other component (e.g., excipient, therapeutic agent, microbe, cargo, and/or biological system) is present in formulations at a concentration (by weight, volume, or concentration) of from about 0.0001% to about 0.99.9

In some embodiments, formulations include one or more excipients. In some embodiments, formulation may not include an excipient. As used herein, the term "excipient" refers to any substance included in a composition with an active agent or primary component, often serving as a carrier, diluent, or vehicle for the active agent or primary component. In some embodiments, excipients may be compounds or compositions approved for use by the US Food and Drug Administration (FDA). In some embodiments, formulation may include excipients that increase stability or stability of one or more other components. Some formulations may include an excipient that modulates payload release. Excipients may include, but are not limited to, solvents, diluents, liquid vehicles, dispersion or suspension media or aids, surfactants, thickening agents, emulsifying agents, lipids, liposomes, isotonic agents, buffers, and preservatives. In some embodiments, excipients include lipidoids, lipid nanoparticles, polymers, lipoplexes, particles, core-shell nanoparticles, peptides, proteins, cells, hyaluronidase, and/or nanoparticle mimics. In some embodiments, processed silk may be used as an excipient. In some embodiments, excipients included in formulations are selected from one or more of sucrose, lactose, phosphate salts, sodium chloride, potassium phosphate monobasic, potassium phosphate dibasic, sodium phosphate dibasic, sodium phosphate monobasic, polysorbate 80, phosphate buffer, phosphate buffered saline, sodium hydroxide, sorbitol, mannitol, lactose USP, Starch 1500, microcrystalline cellulose, potassium chloride, sodium borate, boric acid, sodium borate decahydrate, magnesium chloride hexahydrate, calcium chloride dihydrate, sodium hydroxide, Avicel, dibasic calcium phosphate dehydrate, tartaric acid, citric acid, fumaric acid, succinic acid, malic acid, hydrochloric acid, polyvinylpyrrolidone, copolymers of vinylpyrrolidone and vinyl acetate, hydroxypropylcellulose, hydroxyethylcellulose, hydroxypropylmethylcellulose, polyvinyl alcohol, polyethylene glycol, acacia, and sodium carboxymethylcellulose. Excipients may include phosphate buffered saline or TRIS buffer. Excipients may be present in formulations at any concentration.

In some embodiments, excipients included in formulations, such as ocular formulations, may be selected from one or more of sorbitol, triethylamine, 2-pyrrolidone, alpha-cyclodextrin, benzyl alcohol, beta-cyclodextrin, dimethyl sulfoxide, dimethylacetamide (DMA), dimethylformamide, ethanol, gamma-cyclodextrin, glycerol, glycerol formal, hydroxypropyl beta-cyclodextrin, Kolliphor® 124, Kolliphor® 181, Kolliphor® 188, Kolliphor® 407, Kolliphor® EL, Cremophor® EL)=, Cremophor® RH 40, Cremophor® RH 60, dalpha-tocopherol, PEG 1000 succinate, polysorbate 20, polysorbate 80, Solutol® HS 15, sorbitan monooleate, poloxamer-407, poloxamer-188, Labrafil® M-1944CS, Labrafil® M-2125CS, Labrasol®, Gellucire® 44/14, Softigen® 767, mono- and di-fatty acid esters of PEG 300, PEG 400, or PEG 1750, Kolliphor® RH60, N-methyl-2-pyrrolidone, castor oil, corn oil, cottonseed oil, olive oil, peanut oil, peppermint oil, safflower oil, sesame oil, soybean oil, hydrogenated vegetable oils, hydrogenated soybean oil, medium chain triglycerides of coconut oil, medium chain triglycerides of palm seed oil, beeswax, d-alpha-tocopherol, oleic acid, medium-chain mono-glycerides, medium-chain di-glycerides, alpha-cyclodextrin, betacyclodextrin, hydroxypropyl-beta-cyclodextrin, sulfo-butylether-beta-cyclodextrin, hydrogenated soy phosphatidylcholine, distearoylphosphatidylglycerol, L-alphadimyristoylphosphatidylcholine, L-alpha-dimyristoylphosphatidylglycerol, PEG 300, PEG 300 caprylic/capric glycerides (Softigen® 767), PEG 300 linoleic glycerides (Labrafil® M-2125CS), PEG 300 oleic glycerides (Labrafil® M-1944CS), PEG 400, PEG 400 caprylic/capric glycerides (Labrasol®), polyoxyl 40 stearate (PEG 1750 monosterate), polyoxyl 8 stearate (PEG 400 monosterate), polysorbate 20, polysorbate 80, polyvinyl pyrrolidone, propylene carbonate, propylene glycol, Solutol® HS15, sorbitan monooleate (Span® 20), sulfobutylether-beta-cyclodextrin, transcutol, triacetin, 1-dodecylazacyclo-heptan-2-one, caprolactam, castor oil, cottonseed oil, ethyl acetate, medium chain triglycerides, methyl acetate, oleic acid, safflower oil, sesame oil, soybean oil, tetrahydrofuran, glycerin, and PEG 4 kDa. Such formulations may include hydrogels. In some embodiments, formulations include one or more of polysorbate 80, poloxamer-188, PEG 4 kDa, and glycerol.

Excipients include pharmaceutically acceptable excipients. The phrase "pharmaceutically acceptable" as used herein, refers to suitability within the scope of sound medical judgment for contacting subject (e.g., human or animal) tissues and/or bodily fluids with toxicity, irritation, allergic response, or other complication levels yielding reasonable benefit/risk ratios. As used herein, the term "pharmaceutically acceptable excipient" refers to any ingredient, other than active agents, that is substantially nontoxic and non-inflammatory in a subject. Pharmaceutically acceptable excipients may include, but are not limited to, solvents, dispersion media, diluents, inert diluents, buffering agents, lubricating agents, oils, liquid vehicles, dispersion or suspension aids, surface active agents, isotonic agents, thickening or emulsifying agents, preservatives, and the like, as suited to the particular dosage form desired. Various excipients for formulating pharmaceutical compositions and techniques for preparing the composition are known in the art (see Remington: The Science and Practice of Pharmacy, 21st Edition, A. R. Gennaro, Lippincott, Williams & Wilkins, Baltimore, MD, 2006; incorporated herein by reference in its entirety). The use of a conventional excipient medium may be contemplated within the scope of the present disclosure, except insofar as any conventional excipient medium may be incompatible with a substance or its derivatives, such as by producing any undesirable biological effect or otherwise interacting in a deleterious manner with any other component(s) of pharmaceutical compositions.

In some embodiments, excipients may include preservatives. As used herein a "preservative" is any substance that protects against decay, decomposition, or spoilage. Preservatives may be natural or synthetic. They may be antimicrobial preservatives, which inhibit the growth of bacteria or fungi, including mold, or antioxidants such as oxygen absorbers, which inhibit the oxidation of food constituents. Common antimicrobial preservatives include calcium propionate, sodium nitrate, sodium nitrite, sulfites (sulfur dioxide, sodium bisulfite, potassium hydrogen sulfite, etc.) and disodium EDTA. Antioxidants include BHA and BHT. Other preservatives include formaldehyde (usually in solution), glutaraldehyde (kills insects), vitamin A, vitamin C, vitamin E, selenium, amino acids, methyl paraben, propyl paraben, potassium sorbate, sodium chloride, ethanol, phenol, m-cresol, p-cresol, o-cresol, chlorocresol, benzyl alcohol, phenylmercuric nitrite, phenoxyethanol, methylchloroisothiazolinone, chlorobutanol, magnesium chloride (e.g., hexahydrate), alkylparaben (methyl, ethyl, propyl, butyl and the like), benzalkonium chloride, benzethonium chloride, sodium dehydroacetate, thimerosal, and combinations thereof. Preservatives may also be a stabilizer. Stabilizers comprise a variety of compounds that are able to maintain the function and activity of other ingredients such as, for example, active ingredients, fragrances and essential oils. In this group there are also several agents that are used for stabilizing the pH value thereby avoiding excessive acidity or alkalinity. A balanced pH value is particularly important for creating stable emulsions.

In some embodiments, excipients may include skin protectants. As used herein skin protectants may be any substance that generally supports or affects skin. Skin protectants may be used for the treatment of minor cuts, scrapes, minor burns, chapped skin and lips, and rashes due to poison ivy, poison oak, poison sumac, and insect bites.

In some embodiments, excipients may include sunscreens. As used herein sunscreens may be any substance that generally supports or affects skin. Ultraviolet (UV) radiation is known to produce erythema and pigmentation on the skin. When directly exposed to the sun, there is 10 to 100 times more exposure of UVA than UVB. UVB (considered the Burning Ray) has an immediate, harmful impact on the skin within minutes. UVA (considered the Aging Ray), which you do not feel, has been shown to damage the skin by penetration deeply into the dermis able of producing premature aging, and wrinkles. Sunscreens are inactive ingredients that are able, however, to avoid chemically or physically UV radiations (UVA and UVB) to penetrate the skin layers. Chemical sunscreens act by absorbing UV-light. Physical sunscreens reflect or scatter light in both the visible and UV-spectrum. Effectiveness of sunscreens depends upon their UV-absorption, concentration, formulation, and ability to withstand swimming or sweating.

In some embodiments, excipients may include pH adjusters. As used herein pH may be any substance that generally can be added to cosmetics or other consumer products, or may otherwise affect skin or hair. pH adjusters are ingredients used to adjust the pH (acidity or alkalinity) of a finished product. The optimum pH for most products is between 4.5 and 7. The ingredients used in a formula sometimes combine to form too acidic or too alkaline of a solution for the skin or scalp. A pH adjuster is then used to either raise or lower the pH to be less irritating to the skin.

In some embodiments, formulations may be included as or in device components. As used herein, the term "device" refers to any article constructed or modified to suit a particular purpose. Devices may be designed for a variety of purposes, including, but not limited to, therapeutic applications, material science applications, and agricultural applications. In some embodiments, processed silk or formulations are embedded or incorporated into devices. Some devices include processed silk or formulations as coatings or lubricants. In some embodiments, devices include implants, patches, mesh, sponges, grafts, insulators, pipes, prosthetics, resistors, bedding, blankets, liners, ropes, plugs, fillers, electronic devices, mechanical devices, medical devices, surgical devices, veterinary devices, and agricultural devices. Additional devices are described herein.

Ocular formulations, for example, may be hydrogels. The ocular formulations may have an osmolarity of from about 1 mOsm to about 1000 mOsm.

In some embodiments, ocular formulation may demonstrate the effects of interfacial viscosity. In some embodiments, the processed silk of an ocular formulation may migrate to the air-water boundary. In some embodiments this migration may result in an increase in the local concentration at this interface and ultimately generate the effects of interfacial viscosity. The effects of interfacial viscosity may be independent of the concentration of processed silk. In some embodiments, the effects of interfacial viscosity may be mitigated through the incorporation of a surfactant. The surfactant may be any surfactant described herein.

In some embodiments, the processed silk may be formulated for topical administration. In some embodiments, the processed silk may be formulated for ocular administration. In some embodiments, the processed silk is formulated for intraocular administration. In some embodiments, the processed silk is formulated for one or more of intravitreal administration, intraretinal administration, intracorneal administration, intrascleral administration, lacrimal administration, punctal administration, administration to the anterior sub-Tenon's, suprachoroidal administration, administration to the posterior sub-Tenon's, subretinal administration, administration to the fornix, administration to the lens, administration to the anterior segment, administration to the posterior segment, macular administration, and intra-aqueous humor administration.

In some embodiments, ocular formulations may be used as artificial tears. In some embodiments, ocular formulations may be used in the management of glaucoma. In some aspects, the ocular formulations useful for the management of glaucoma may be in the format of drops. Eye drops used in managing glaucoma help the eye's fluid to drain better and decrease the amount of fluid made by the eye which decreases eye pressure. Ocular formulations formatted as eye drops may include prostaglandin analogs, beta blockers, alpha agonists, and carbonic anhydrase inhibitors.

In some embodiments, formulations formatted as drops may be used to treat ocular allergies. Drops may contain histamine antagonists or nonsteroidal anti-inflammatory drug (NSAIDs), which suppress the optical mast cell responses to allergens including (but not limited to) aerosolized dust particles.

In some embodiments, formulations formatted as drops may be used to treat conjunctivitis or pink eye. In some embodiments ocular formulations comprising antibiotics as therapeutic agents may be prescribed when the conjunctivitis is caused by bacteria. In some embodiments, pharmaceutical compositions comprising ocular formulations may be prepared as artificial tears to help dilute irritating allergens present in the tear film.

In some embodiments, ocular formulations formatted as drops may include mydriatics, an agent that causes pupil dilation. Mydriatics include but are not limited to phenylephrine, cyclopentolate, tropicamide, hydroxyamphetamine/tropicamide, atropine, cyclopentolate/phenylephrine ophthalmic, homatropine ophthalmic, and scopolamine. Such formulations may be used in the treatment of ocular indications or in preparation for the diagnosis of ocular conditions.

In some embodiments, ocular formulations formatted as solutions may be used as contact lens solution. Contact lens solutions are solutions used for the storage of contact lenses in between use of said contact lenses. Contact lenses may be used for vision correction and/or for cosmetic purposes. In some embodiments, the anti-microbial and/or bacteriostatic properties of a formulation may enable the storage of contact lenses while prohibiting the growth of microbes and/or bacteria.

In some embodiments, pharmaceutical compositions that include processed silk may be administered at a dose sufficient to provide a therapeutically effective amount of therapeutic agents or processed silk. As used herein, the term "therapeutically effective amount" refers to an amount of an agent sufficient to achieve a therapeutically effective outcome. As used herein, the term "therapeutically effective outcome" refers to a result of treatment where at least one objective of treatment is met. In some embodiments, a therapeutically effective amount is provided in a single dose. In some embodiments, a therapeutically effective amount is administered according to a dosing schedule that includes a plurality of doses. Those skilled in the art will appreciate that in some embodiments, a unit dosage form may be considered to include a therapeutically effective amount of a particular agent or entity if it includes an amount that is effective when administered as part of such a dosage regimen.

Consumer Product Applications

In some embodiments, formulations may be used to produce or may be incorporated into consumer products. As used herein, the term "consumer products" refers to goods or merchandise purchasable by the public. Consumer products may include, but are not limited to, agricultural products, therapeutic products, veterinary products, and products for household use. Non-limiting examples of consumer products include cleaning supplies, sponges, brushes, cloths, protectors, sealant, adhesives, lubricants, protectants, labels, paint, clothing, insulators, devices, bandages, screens, electronics, batteries, and surfactants.

In any embodiment of consumer products, for personal or non-personal use, the following are non-limiting examples of suitable ranges for various parameters in and for preparation of the silk products of the present disclosure. The silk products of the present disclosure may include one or more, but not necessarily all, of these parameters and may be prepared using various combinations of ranges of such parameters.

The details of one or more embodiments of the disclosure are set forth in the accompanying description below. Although any materials and methods similar or equivalent to those described herein can be used in the practice or testing of the present disclosure, the preferred materials and methods are now described. Other features, objects and advantages of the disclosure will be apparent from the description. In the description, the singular forms also include the plural unless the context clearly dictates otherwise. Unless defined otherwise, all technical and scientific terms used herein have the same meaning as commonly understood by one of ordinary skill in the art to which this disclosure belongs. In the case of conflict, the present description will control.

The present disclosure is further illustrated by the following non-limiting examples.

EXAMPLES

Example 1

Characterization of Processed Silk Formulations

Stock Solution Characterization: Silk fibroin was purified by degumming raw silk yarn in 0.5 M sodium carbonate at 85° C. for either 240 or 360 minutes; dissolving in 9.3M lithium bromide at 60° C. for 16 hours (overnight), and purifying by TFF using a regenerated cellulose or polyethersulfone filter, and concentrating and recovering processed silk fibroin from the TFF.

10% (w/v) purified silk fibroin in water was used in 4 stock solutions for formulation preparations that did not include any buffers or salts. Characteristics of the solutions are provided in Table 1. The average molecular weight (MW) was determined by SEC-UPLC-UV, and concentration by gravimetry. Additionally the solutions underwent elemental analysis to determine the final lithium (Li) and bromide (Br) content and those results are also provided in Table 1. The levels of arsenic, cadmium, cobalt, lead and nickel were also evaluated and were all below detectable levels or at low levels (0.3 ppm for cobalt for solution 3).

TABLE 1

STOCK SOLUTION - CHARACTERISTICS

| Solution No. | Average MW (kDa) | Concentration (w/v) | pH | Osmolality (Freezing Pt. Depression) | Density (g/mL) | Transmittance (OD600) | Lithium (ppm) | Bromide (ppm) |
|---|---|---|---|---|---|---|---|---|
| Soln. 1 | 41.9 | 7.6% | 8.6 | 32 | 1.02 | 96.1% | 132 | 1.8 |
| Soln. 2 | 40.0 | 9.2% | 8.4 | 37 | 1.02 | 99.9% | 163 | 1.6 |
| Soln. 3 | 40.9 | 10.1% | 7.9 | 43 | 1.03 | 98.6% | 163 | 5.8 |
| Soln. 4 | 30.1 | 10.3% | 8.7 | 48 | 1.03 | 99.7% | 205 | 3.8 |

In order to determine if any of the stock solutions contained bacteria, yeast, mold or fungi, the stock solutions underwent microbiology testing (USP 61 and USP 62). The samples were run at 1:10 dilution and none of the batches showed any presence of bacteria, yeast, mold or fungi.

As silk displays unique shear viscosity properties (increasing viscosity with decreasing shear rate and maintaining viscosity across a wide dilution range), the viscosity of the stock solutions was evaluated using rotational rheology and the results are shown in Table 2. The shear viscosity of silk fibroin solutions increases with decreasing molecular weight. Interfacial viscosity was also evaluated using a rotational rheometer and the silk solutions displayed higher viscosity and yield stress at lower shear rates.

TABLE 2

STOCK SOLUTION - SHEAR VISCOSITY

| Solution No. | Stock Solution Viscosity (mPa*s) | 2% Silk Fibroin Viscosity (mPa*s) |
|---|---|---|
| Soln. 1 | 61.4 | 85.4 |
| Soln. 2 | 79.8 | 34.0 |
| Soln. 3 | 57.5 | 24.4 |
| Soln. 4 | 112.5 | 58.7 |

Stability of Processed Silk Solutions: Four solutions (0.5% or 1% w/v in PBS at a pH 7.4) of silk of varying molecular weight (20, 30, 75 and 110 kDa) were evaluated to determine the effect of the autoclave process on molecular weight of the processed silk in the solutions. Molecular weight was evaluated by UPLC-SEC, viscosity by rheology, surface spreading by lycopodium and agitation stability was also evaluated.

Stability: The lower molecular weight silk fibroin solutions (1%) remained clear through the autoclave process. The high molecular weight silk (75-110 kDa) had precipitation post autoclave and a 70-80% reduction in molecular weight. The low molecular weight silk (20-35 kDa) did not have any precipitation post autoclave and a 45-50% reduction in molecular weight.

Viscosity: Interfacial viscosity maintained or improved after terminal autoclave of the solutions. All formulations (0.5% and 1% in PBS) maintained above minimal viscosity limit (30 cPs), trended toward increasing viscosity with decreasing molecular weight and the surface spreading was maintained post-autoclave.

Stability of Low Molecular Weight Processed Silk Solutions: Silk solutions of 0.1%, 0.3%, 0.5%, 1.0% and 3.0% of either 9 kDa, 17 kDa, 20 kDa or 30 kDa silk in PBS were evaluated to determine the effect of the autoclave process on stability of the solutions. The lower molecular weight solutions in PBS displayed improved stability at lower concentration post autoclave. The silk solutions were agitated at room temperature and all the solutions of the 9 kDa silk remained clear, the 0.5%, 1.0% and 3.0% solutions of 17 kDa silk remained clear and the 1.0% and 3.0% solutions of the 20 kDa and 30 kDa remained clear. Therefore, the 9 kDa and 17 kDa silk solutions showed improved stability post autoclave.

Stability of Processed Silk Solutions with Buffers: To determine the effect of buffers on silk stability after the autoclave process, solutions of processed silk and buffers were analyzed before and after each of two autoclave cycles.

Silk solutions at 2% (w/v) silk fibroin at 40.5 kDa or 30.0 kDa were made in a variety of different buffer and salt combinations (no buffer, 25 mM phosphate buffer, 25 mM TRIS buffer, 25 mM citrate buffer, 25 mM borate buffer, and 25 mM carbonate buffer, all with or without 135 mM sodium chloride for 24 total groups) at a pH of 7.4-7.5. Individual glass vials were then filled (as close to 0% headspace as possible) with each sample and autoclaved at 121° C. for 30 minutes on a liquid cycle. After briefly cooling, samples were assessed for visual evidence of precipitation or gelling, pH, and average molecular weight via UPLC-SEC. Samples were then left at 4° C. for about a week. Then the same samples were autoclaved again (this time with roughly 25% headspace) for the same duration and type of cycle. After briefly cooling, the samples were assessed for the same characteristics. The results were then compared back to initial pH and representative molecular weight measurements prior to autoclaving. The molecular weight for each solution is provided in Tables 3 and 4.

TABLE 3

40.5 KDA SILK SOLUTIONS

| Buffer (25 mM) | Post Autoclave Cycle 1 | % Hydrolysis | Observations | Post Autoclave Cycle 2 | % Hydrolysis | Observations |
|---|---|---|---|---|---|---|
| Water | 30.4 | 25% | Slight precipitation | — | — | Clear gel with slight precipitation |
| Phosphate | 18.7 | 54% | Very slight precipitate | 14.9 | 63% | Precipitate, slightly thickened |
| TRIS | 33.0 | 19% | Very slight precipitate, slightly hazy | 32.3 | 20% | Slight precipitate |
| Borate | 29.3 | 28% | Slight precipitate, | — | — | Clear gel with slight precipitation |
| Citrate | 26.4 | 35% | Very slight precipitate, slightly thickened | — | — | Slightly hazy gel with slight precipitation |
| Carbonate | 19.8 | 51% | Slight precipitate | 14.9 | 63% | Very slight precipitate, slight yellow color |
| NaCl | 30.8 | 24% | Very slight precipitate | — | — | Runny clear gel with slight precipitation |

TABLE 3-continued 40.5 KDA SILK SOLUTIONS

| Buffer (25 mM) | Post Autoclave Cycle 1 | % Hydrolysis | Observations | Post Autoclave Cycle 2 | % Hydrolysis | Observations |
|---|---|---|---|---|---|---|
| Phosphate + NaCl | 20.0 | 51% | Very slight precipitate | — | — | Runny clear gel with slight precipitation |
| TRIS + NaCl | 33.1 | 18% | Very slight precipitate, slightly hazy | — | — | Slightly hazy solution with cloudy gel globules |
| Borate + NaCl | 29.7 | 27% | Very slight precipitate, slightly hazy | — | — | Runny gel with slight precipitation |
| Citrate + NaCl | 27.3 | 33% | Very slight precipitate, slightly thickened | — | — | Slightly hazy gel with slight precipitation |
| Carbonate + NaCl | 19.8 | 51% | Very slight precipitate | 15.1 | 63% | Slight precipitate with cloudy globules |

TABLE 4

30.0 KDA SILK SOLUTIONS

| Buffer (25 mM) | Post Autoclave Cycle 1 | % Hydrolysis | Observations | Post Autoclave Cycle 2 | % Hydrolysis | Observations |
|---|---|---|---|---|---|---|
| Water | 23.4 | 22% | Slight precipitate | — | — | Weak clear gel |
| Phosphate | 16.4 | 45% | Slight precipitate | 13.7 | 54% | Precipitate, slightly thickened |
| TRIS | 24.8 | 17% | Very slight precipitate | 25.1 | 16% | Very slight precipitate, some drying |
| Borate | 22.6 | 25% | Slight precipitate | — | — | Weak clear gel |
| Citrate | 21.0 | 30% | Slight precipitate | — | — | Clear gel with slight precipitation |
| Carbonate | 16.8 | 44% | Very slight precipitate | 13.5 | 55% | Some precipitate, slight yellow color |
| NaCl | 23.1 | 23% | Almost no precipitate | — | — | Weak gel with slight precipitation |
| Phosphate + NaCl | 17.2 | 43% | Very slight precipitate | 14.7 | 51% | Slight precipitate |
| TRIS + NaCl | 24.8 | 17% | Very slight precipitate | 24.8 | 17% | Slight precipitate |
| Borate + NaCl | 22.8 | 24% | Very slight precipitate | 22.0 | 27% | Very slight precipitate |
| Citrate + NaCl | 21.5 | 28% | Very slight precipitate | — | — | Weak gel with slight precipitation |
| Carbonate + NaCl | 17.4 | 42% | Very slight precipitate | 13.9 | 54% | Very slight precipitate, slight yellow color |

Through the first autoclave cycle all formulations remained clear. The pH of carbonate and citrate solutions were elevated. For TRIS and borate solution hydrolysis was reduced and the addition of NaCl had little effect as compared to the solutions without NaCl. After the second autoclave cycle most of the formulations in the 40.5 kDa solutions gelled but the solutions with TRIS remained clear and the molecular weight was stable. Most of the 30.0 kDa solutions did not gel after the second autoclave cycle and the TRIS and borate solutions performed the best after the second cycle.

The lower molecular weight silk fibroin solutions was found to be more stable through the autoclave as compared to the higher molecular weight solutions. The viscosity and surface activity were maintained or enhanced post autoclave and silk fibroin hydrolysis was observed in all buffers with or without NaCl. Additionally, TRIS buffer most consistently reduced silk hydrolysis, precipitation and gelation through autoclave cycles.

then compared back to representative molecular weight measurements prior to autoclaving. The molecular weight for each solution is provided in Table 5.

TABLE 3

KDA SILK SOLUTIONS

| Buffer (25 mM) | Pre-Autoclave | Post Autoclave Cycle 1 | % Hydrolysis | Observations | Post Autoclave Cycle 2 | % Hydrolysis | Observations |
|---|---|---|---|---|---|---|---|
| Phosphate + NaCl | 32.5 kDa | 17.4 kDa | 46% | Very slight precipitate, needles | 12.6 kDa | 61% | White flaky precipitate |
| TRIS + NaCl | 32.5 kDa | 26.9 kDa | 17% | Very slight precipitate, needles | 24.1 kDa | 26% | White flaky precipitate |
| Borate + NaCl | 32.5 kDa | 23.4 kDa | 28% | Very slight precipitate, needles | 19.4 kDa | 40% | White flaky precipitate |
| Phosphate + KCl | 31.6 kDa | 17.0 kDa | 46% | Very slight precipitate, needles | 12.6 kDa | 60% | Very slight precipitate, needles |
| TRIS + KCl | 32.5 kDa | 26.9 kDa | 17% | Very slight precipitate, needles | 23.5 kDa | 28% | Minimal white, flaky precipitate |
| Borate + KCl | 32.5 kDa | 22.9 kDa | 30% | Very slight precipitate, needles | 20.0 kDa | 38% | White flaky precipitate |

Lyophilized and Milled Silk Fibroin Powders to Create Solutions: In order to create silk solutions from lyophilized and milled silk fibroin powders, dry silk fibroin powder is added to a container. The buffer (water or saline is preferred) is slowly added to the container and allowed to slowly dissolve the powder with no agitation for 3-5 minutes before swirling the container to aid dissolution while trying to avoid high shearing during dissolution.

Example 2

Characterization of Purified Silk Fibroin Formulations Through Autoclave

Silk Fibroin Extraction and Purification: Silk fibroin was purified by degumming raw silk yarn in 0.5 M sodium carbonate at 85° C. for 360 minutes; dissolving in 9.3M lithium bromide at 60° C. for 16 hours (overnight), and purifying by TFF using a regenerated cellulose or polyethersulfone filter, and concentrating and recovering processed silk fibroin from the TFF.

Stability of Processed Silk Solutions with Buffers: To determine the effect of buffers and salt content on silk stability after the autoclave process, solutions of processed silk and buffers were analyzed before and after each of two autoclave cycles.

Formulations at 1% (w/v) silk fibroin were made in a variety of different buffer and salt combinations (no buffer, 25 mM phosphate buffer, 25 mM TRIS buffer, and 25 mM borate buffer, all with either 135 mM sodium chloride or 135 mM potassium chloride for 6 total groups) at a pH of 7.4-7.5. Individual glass vials were then filled with each sample in duplicate, capped, and autoclaved at 121° C. for 30 minutes on a liquid cycle. After briefly cooling, samples were assessed for visual evidence of precipitation or gelling and average molecular weight via UPLC-SEC-UV. Samples were then left at RT overnight before being autoclaved again (this time with roughly 10% headspace) for the same duration and type of cycle. After briefly cooling, the samples were assessed for the same characteristics. The results were Through the first autoclave cycle all formulations remained clear with some very slight precipitation, but no gelling. TRIS buffer formulations showed the lowest level of hydrolysis, followed by borate buffer, with phosphate showing the most hydrolysis. The addition of NaCl or KCl had a similar impact on hydrolysis in all of the buffers. After the second autoclave treatment all of the formulations remained as solutions with no gelling present. Again, TRIS performed the best followed by borate and then phosphate as it pertains to maintenance of silk fibroin molecular weight. NaCl or KCl did not impact the molecular weight in any of the buffers. Precipitation of silk fibroin was present in all formulations after the second autoclave treatment. All formulations containing NaCl, regardless of buffer, displayed a moderate white, flaky precipitate. In the presence of KCl, the precipitate was reduced in both the phosphate and TRIS formulations. The phosphate/KCl formulation displayed the least amount of precipitation with a very slight presence of thin needles of silk, while TRIS/KCl formulations had a minimal amount of a white, flaky precipitate. Borate/KCl displayed a moderate white, flaky precipitate similar to all of the NaCl formulations.

TRIS buffer most consistently reduced silk hydrolysis, followed by borate, and then phosphate buffers through autoclave cycles. NaCl and KCl salts, although they did not impact the hydrolysis of the silk fibroin, impacted the level of precipitation following two autoclave cycles, with KCl reducing precipitation. All the formulations maintained their solution state (did not gel) following two autoclave cycles.

The invention claimed is:
1. A method of preparing a stable, solubilized silk fibroin preparation comprising,
providing a processed silk fibroin preparation, wherein the processed silk fibroin preparation was prepared by degumming a silk starting material, dissolving the degummed silk in 5M to 13M lithium bromide or a mixture of calcium chloride, ethanol and water to provide dissolved silk fibroin, and purifying the dissolved silk fibroin the using dialysis or tangential flow filtration to reduce the lithium bromide or calcium chloride and ethanol and provide the processed silk fibroin preparation;

preparing a solution consisting of 0.1 to 5.0 wt % of the processed silk fibroin preparation in 10 mM to 100 mM aqueous TRIS buffer, pH 5.0 to 9.0 to provide a fibroin solution;

treating the fibroin solution at a first pressure of 15 to 30 psi and a first temperature of 121 to 135° C. for a first time of 1 to 90 min; and optionally treating the fibroin solution at a second pressure of 15 to 30 psi and a second temperature of 121° C. to 135° C. for a second time of 1 to 90 min, to provide the stable, solubilized silk fibroin preparation, wherein the stable, solubilized silk fibroin preparation has a molecular weight that changes by less than 33% during the first and optional second treating step, does not form a gel during the first and optional second treating step, remains clear after the first and optional second treating step, or a combination thereof.

2. The method of claim 1, wherein the stable, solubilized silk fibroin preparation is an aqueous solution comprising 0.1 to 10% weight/volume silk fibroin.

3. The method of claim 1, wherein the first pressure is 15 to 20 psi, the first temperature is 121° C. to 125° C., and the first time is 30 to 45 minutes.

4. The method of claim 1, wherein the second pressure is 15 to 20 psi, the second temperature is 121° C. to 125° C., and the second time is 30 to 45 minutes.

5. The method of claim 1, wherein the 10 mM to 100 mM aqueous TRIS buffer further comprises 10 mM to 100 mM KCl or NaCl.

6. The method of claim 1, wherein the stable, solubilized silk fibroin preparation has a molecular weight that changes by less than 33% after standing at room temperature for at least 30 days, does not form a gel after standing at room temperature for at least 2 years, remains clear after standing at room temperature for at least 2 years, or a combination thereof.

7. The method of claim 1, wherein the processed silk fibroin preparation has a number average molecular weight of 20 to about 50 kDa as determined by size exclusion chromatography.

8. The method of claim 1, wherein the processed silk fibroin preparation has a number average molecular weight of 25 to about 42 kDa as determined by size exclusion chromatography.

9. A method of preparing a stable, solubilized silk fibroin preparation comprising, providing a processed silk fibroin preparation, wherein the processed silk fibroin preparation was prepared by degumming a silk starting material, dissolving the degummed silk in 5M to 13M lithium bromide or a mixture of calcium chloride, ethanol and water to provide dissolved silk fibroin, and purifying the dissolved silk fibroin the using dialysis or tangential flow filtration to reduce the lithium bromide or calcium chloride and ethanol and provide the processed silk fibroin preparation;

preparing a solution consisting of 0.1 to 5.0 wt % of the processed silk fibroin preparation in 10 mM to 100 mM aqueous TRIS buffer, pH 5.0 to 9.0, with 100 mM to 200 mM KCl or NaCl, to provide a fibroin solution;

treating the fibroin solution at a first pressure of 15 to 30 psi and a first temperature of 121° C. to 135° C. for a first time of 1 to 90 min; and optionally treating the fibroin solution at a second pressure of 15 to 30 psi and a second temperature of 121° C. to 135° C. for a second time of 1 to 90 min, to provide the stable, solubilized silk fibroin preparation, wherein the stable, solubilized silk fibroin preparation has a molecular weight that changes by less than 33% during the first and optional second treating step, does not form a gel during the first and optional second treating step, remains clear after the first and optional second treating step, or a combination thereof.

* * * * *